(12) United States Patent
Vanscoy Barnett

(10) Patent No.: US 9,398,880 B2
(45) Date of Patent: Jul. 26, 2016

(54) PLURALITY OF LAMINATION FOR SOFT TISSUE COMPRESSION SUPPORT, PROTECTION AND BRACING; INTELLIGENT TEXTILE FOR EQUINE AND EQUESTRIAN SPORTS OR ACTIVITIES

(71) Applicant: Kelly Annette Vanscoy Barnett, Bend, OR (US)

(72) Inventor: Kelly Annette Vanscoy Barnett, Bend, OR (US)

( * ) Notice: Subject to any disclaimer, the term of this patent is extended or adjusted under 35 U.S.C. 154(b) by 362 days.

(21) Appl. No.: 13/847,982

(22) Filed: Mar. 20, 2013

(65) Prior Publication Data

US 2014/0288383 A1    Sep. 25, 2014

(51) Int. Cl.
*A61H 1/00* (2006.01)
*A61B 5/00* (2006.01)
*G01N 27/00* (2006.01)
*A41D 13/05* (2006.01)
*A61B 5/11* (2006.01)

(52) U.S. Cl.
CPC ............. *A61B 5/48* (2013.01); *A41D 13/0543* (2013.01); *A61B 5/11* (2013.01); *A61B 5/6801* (2013.01); *G01N 27/00* (2013.01); *A61B 5/112* (2013.01); *A61B 5/6828* (2013.01); *A61B 2503/10* (2013.01); *A61B 2503/40* (2013.01); *A61B 2562/0219* (2013.01); *A61B 2562/0247* (2013.01); *A61B 2562/0271* (2013.01)

(58) Field of Classification Search
CPC ..................... A61F 13/06–13/069; A61D 9/00
USPC ............................... 600/300–301; 602/42–46
See application file for complete search history.

(56) References Cited

U.S. PATENT DOCUMENTS

| | | | | |
|---|---|---|---|---|
| 5,735,807 | A * | 4/1998 | Cropper | 602/63 |
| 6,050,967 | A * | 4/2000 | Walker et al. | 602/75 |
| 6,723,967 | B2 * | 4/2004 | Rock et al. | 219/528 |
| 2004/0031246 | A1 * | 2/2004 | Springs | 54/82 |
| 2005/0192524 | A1 * | 9/2005 | Lipshaw et al. | 602/62 |
| 2006/0255433 | A1 * | 11/2006 | Xu | 257/643 |
| 2008/0015483 | A1 * | 1/2008 | Kilbey | 602/53 |
| 2008/0033506 | A1 * | 2/2008 | Flick | 607/50 |
| 2010/0268111 | A1 * | 10/2010 | Drinan et al. | 600/547 |
| 2010/0286950 | A1 * | 11/2010 | Heijkants et al. | 702/151 |
| 2011/0092927 | A1 * | 4/2011 | Wilkes et al. | 604/304 |

* cited by examiner

*Primary Examiner* — William Thomson
*Assistant Examiner* — Marie Archer

(57) ABSTRACT

A Wearable Orthopedic/Orthotic Device for diagnostics and therapy of an equine limb comprises a soft tissue compression material and a sheet of stretchable laminate material for soft tissue compression and bracing. The device includes a stretchable, porous and breathable polyurethane membrane to allow a certain degree of perspiration and heat to escape while retaining a therapeutic amount of heat. The device includes an intelligent textile layer, including fibertronics, organic electronics, other forms of e-textiles and sensors for monitoring parameters associated with tendon and ligament injuries in sub clinical time periods. The device may include an acoustic sensor for detecting the speed and frequency of sound traveling through underlying tissue onto which an acoustic signal is emitted. In a diagnostic monitoring method, parameters associated with the health tissue of the equine limb and body is wirelessly transmitted by the device to an external receiver for analysis.

11 Claims, 11 Drawing Sheets

INVENTION EMBODIMENT FOR NORMAL JOINT EVALUATION/ PHYSIOLOGICAL PARAMETERS.

INVENTION EMBODIMENT FOR PRESSURE MATRIX FOR FITTING PROSTHETICS/WRAPPINGS.

WIRELESS SIGNAL
EXAMPLE OF A PORTABLE INTERFACE OPTION FOR PROGRAMMING, DATA COLLECTING AND CONFIGURING.

PUL FOAM OR FILM
NEOPRENE
TOP AND BOTTOM
MOISTURE
HEAT

PUL LAMINATE IS THINNER, STRONGER AND
BREATHABLE AND HYPOALERGENIC.

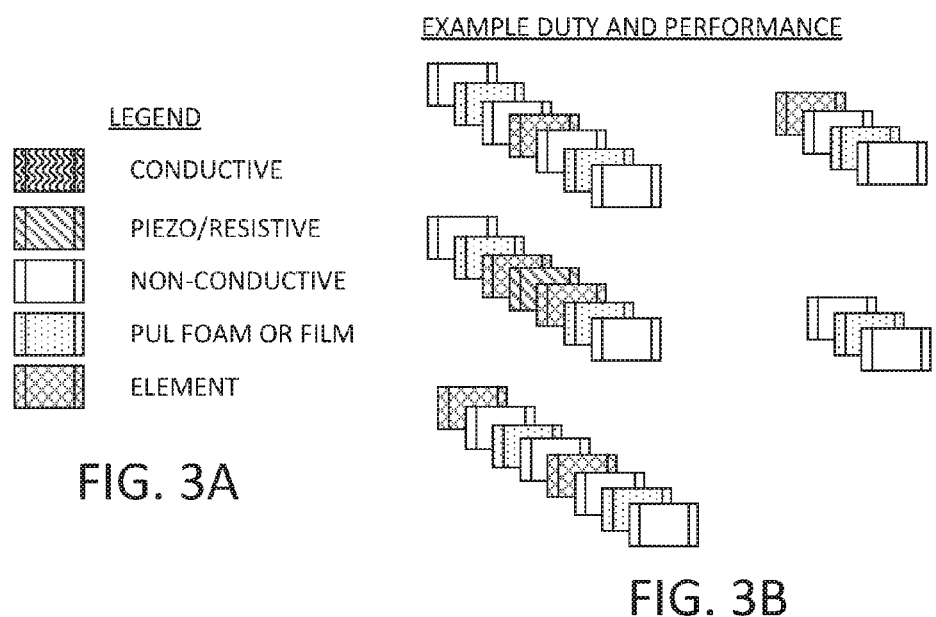
FIG. 3A
FIG. 3B
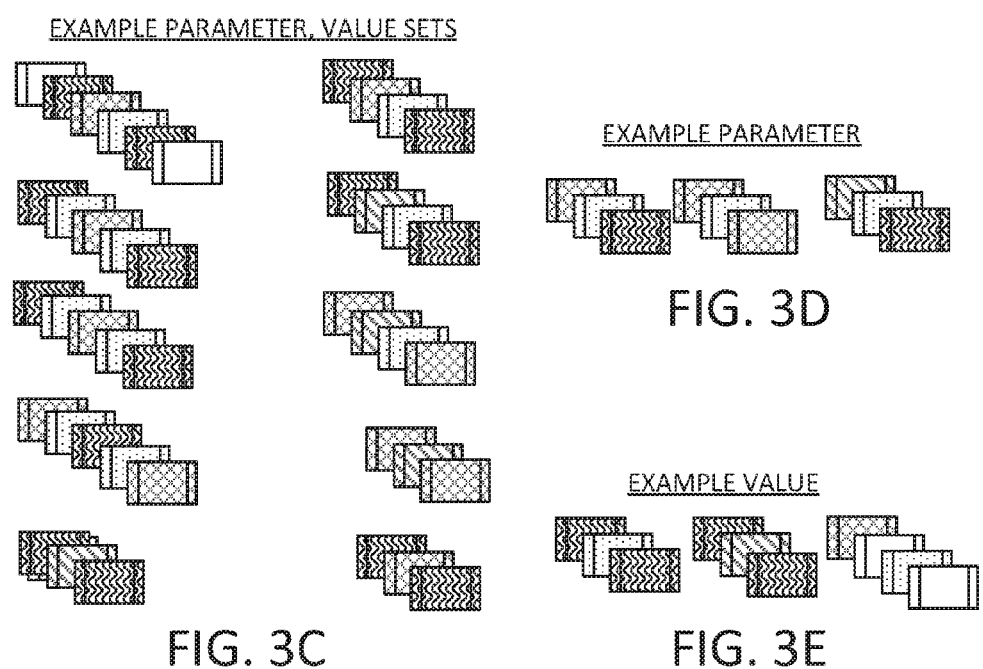
FIG. 3C
FIG. 3D
FIG. 3E

LEGEND
- ▨ PLURALITY OF LAMINATION
- ▦ EMBEDDED ELEMENT
- ▧ CONDUCTIVE
- ▨ PIEZO/RESISTIVE
- ☐ NON-CONDUCTIVE
- ▨ PUL FOAM OR FILM
- ▨ ELEMENT
- △ PUL FOAM OR FILM
- ▭ ELEMENT
FIG. 6A
PLURALITY OF LAMINATION EXAMPLE
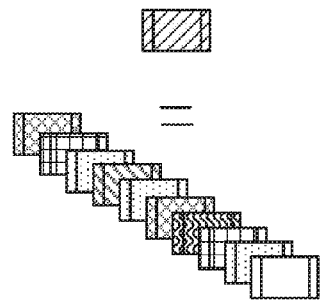
FIG. 6B
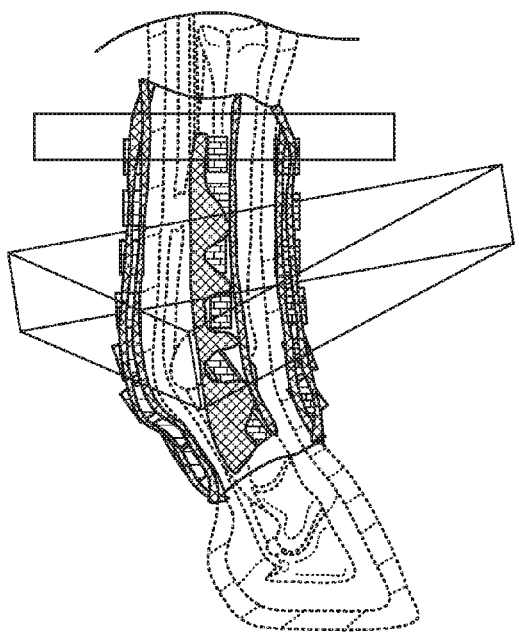
FIG. 6C
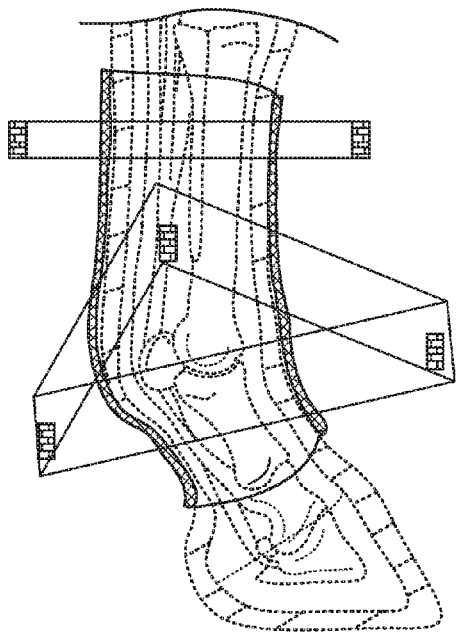
FIG. 6D

AVERAGE HUMAN MALE

RUNNING STRIKE = 55 PSI

JUMPING STRIKE = 500 PSI

AVERAGE EQUINE

WALKING STRIKE = 500 PSI

RUNNING STRIKE = 5,100 PSI

FIG. 8A

INVENTION EMBODIMENT FOR NORMAL JOINT EVALUATION/ PHYSIOLOGICAL PARAMETERS.

INVENTION EMBODIMENT FOR PRESSURE MATRIX FOR FITTING PROSTHETICS/WRAPPINGS.

WIRELESS SIGNAL
EXAMPLE OF A PORTABLE INTERFACE OPTION FOR PROGRAMMING, DATA COLLECTING AND CONFIGURING.

PLURALITY OF LAMINATION FOR SOFT TISSUE COMPRESSION SUPPORT, PROTECTION AND BRACING; INTELLIGENT TEXTILE FOR EQUINE AND EQUESTRIAN SPORTS OR ACTIVITIES

FIELD OF THE INVENTION

This invention relates to plurality of a laminated textile and elements that are an alternative to neoprene and other materials currently used for equine and equestrian sports medicine, rehabilitation or activity, This laminate is intended to treat or aid in the prevention, recovery, evaluation and treatment of a life-threatening or irreversibly debilitating injury to the equine limb (tendon and ligament that support joint structures and aid in locomotion) that does not have a serious adverse effect associated with an available products for equine supportive, protective and bandaging equipment. Providing an embodiment for end-user to monitor a specified parameter from a parameters list; and providing an interface that allows the user to associate individual parameters from the parameters list with individual values from a values list; thereby describing an item falling within the item classification as a set of parameter-value pairs; providing self-contained or external interface options to prevent serious treatment related side effects associated with current products, product related re-injury and treatment decisions that rely on intuition that may have a detrimental effect on the underlying limb structures.

The concept of the invention could be utilized in real time, real use scenarios and not necessarily in a clinical setting where the subject is attached to devices, wires or on a treadmill or sensing platform. More particularly, but not by way of limitation, the intelligent textile can monitor temperature, detect, send and or receive acoustic emissions; sound cancellation of noise from external environments, fabric bend sensors, tilt sensors for range of motion parameters; determining improved fit of apparel by way of a fabric stretch sensor and the like; safety parameters for areas of concern to proper joint function can be determined or improved; joint and tissue support, health and treatment. The ability to have equines untethered to wires attached to expensive devices reduces the potential for panic which may cause further injury to the equine or damage expensive non-wearable devices such as ultrasound units or phonophoresis devices. An untethered device would include an element for a current source such as but not limited to a battery to obtain functions described within the entirety of this document.

The concept does allow for data collected to be interfaced with existing technology for position, posture gait and motion analysis and methods to improve the understanding of injury prevention, causes and treatment. This concept can be utilized outside of the equine and equine sport or activity to encompass all sports. The plurality of textile is a method for apparatus development.

BACKGROUND OF THE INVENTION

In this document, the terms used to describe embodiments are used in their plain-English equivalents without instance or usage per common patent documents. Therefore, the descriptions below are meant to be open-ended, that is, a system, device, article, or process that includes elements in addition to those listed are still deemed to fall within the scope of a claim and are not meant to be limiting in nature.

Repetitive-use, sports and occupational related distal limb injury is one of the leading causes of lameness and death among equine athletes. Incidence of lameness from all causes; repetitive-use or other sports related injury, occupational or mechanical injuries, is estimated to be 9-14 occurrences per year for every 100 equines. Other joints of locomotion are also in need of protection and support and therefore are not excluded from potential injury. Scientific Research shows materials that are in current use (neoprene, leather, hard polyurethane, rigid or semi-rigid) for the protection of equine distal limbs suffer from inherent flaws that increase the risk of injury to soft tissues. These risks include heat damage, allergic reactions, and strain from weight and/or mechanical injuries, see FIG. 7. Some risk of use comes from utility design and others are from textile characteristics. The material described here-in is particularly suited for the prime athlete or to return a previously injured athlete to duty, see FIG. 2D, as the properties of this material mitigate or eliminate said character flaws to prevent harm and aid in reducing pain, edema reduction, increase proprioception and assist with joint stabilization, FIG. 2C.

Several patents have been filed disclosing various systems of bracing equine limb joints. While many are still commercially available such as U.S. Pat. No. 5,871,458 (Detty), U.S. Pat. No. 5,115,627 (Scott), U.S. Pat. No. 5,579,627 (Vogt), U.S. Pat. No. 5,226,191 (Mitchell) and US2009/0288377 (Heid), the prior art has many disadvantages that need to be overcome. While the foregoing prior art for equine orthotic/bracing systems may be generally suited for their intended purposes, they are not meeting all recommendations for what is generally accepted as safe by scientific researchers. Furthermore, the need for improved resistance to accidental disconnection, strike protection and customization for therapeutic uses are desired.

There are various types of injuries sustained by the equine athlete. Common injuries include, tendonitis from sports related repetitive-use syndromes, contusions from overreaching or striking an object, sprains, strains, torn cartilage and ultimately fractured limbs from soft tissue failure causing the joints to fall apart. These injuries are most common from equines or humans participating in rigorous activities in which they are subjected by training or sporting activities. Providing correct compression, see FIG. 4, has been shown to prevent injuries to soft tissues, increase athletic performance and decrease rehabilitation time.

Both Equine, see FIG. 5A, and Equestrians participating in equine sports or activities can suffer from similar fatigue strains, tears and pain as a result of the sport in which they participate. Equines and humans also share similar biometric parameters for blood pressure. Thus, ranges for safe athletic and therapeutic compression are established. Neoprene boots or orthotics, have been the standard for years to offer compression and protection to the equine limbs to support the distal limb tendon and ligament. However, equines use materials designed to accommodate the weight of a human (FIG. 8A); not designed with the force vector, force vector return to accommodate the forces of equine muscles (FIG. 8B) and tendon/ligament strain (FIG. 8C).

There are many down sides to neoprene products. It is a known allergen to susceptible horses and ponies; however, US Laws do not require a disclosure of such risk, although DuPont recommends it. In 2002 the European Union Dangerous Preparations Directive 1999/45/EC requires the risk to be noted and equine products ordered from the UK have an allergy warning label sewn in the product. For susceptible equines, each exposure increases the reaction. Owners who do not have a better alternative continue to use neoprene products with the presumption that a skin reaction is treatable and a joint failure, despite significant financial outlays often renders the animal unusable or needing to be humanely euthanized.

Due to the bulk of Neoprene, there is a bunching and gathering problem into the joint spaces, see FIG. 7. High-speed photography has captured images of neoprene and other bulky products like leather bunching, binding and migrating around the joints of an equine limb in motion, particularly when a joint is flexed. When the material gathers it becomes non-elastic and in effect loses its athletic compression under the bunch and may bind on the opposing side.

Neoprene and other non-porous materials are hot, see FIG. 2D, cause the skin to sweat and are known to cause overheating injuries to tendon and ligaments. An unprotected animals' tissue heats up naturally to within one degree of temperatures known to cause cellular damage. Applying an insulating layer of Neoprene alone or laminated to other base materials (Neoprene and leather, neoprene and rigid plastics or in an athletic situation creates temperatures that researchers have proven to be unsafe. Perforating Neoprene to add breathability is still comparatively hot, has a short lifecycle, offers lower rupture strength, and offers less compression in comparison.)

The plurality of laminations and elements, see FIG. 3, allows for unprecedented array of parameters and values to be determined for equine apparel with the functionality to monitor for said parameters and values. To illustrate without providing limitation: a parameter and value data sets can signal when therapeutic compression range (parameter) is nearing tolerance (value) and compare this relationally to limb temperature. The limb temperature (value) in relation to acceptable thermal variances (parameter) will also monitor for sufficient arterial blood flow via temperature changes to ensure the limb is being properly perfused in relation to the compressive forces to ensure intermittent or permanent pulse obliteration has not occurred from bend, stretch, flex, force and pressure exerted onto the tissues from the wrap, brace or bandage when the limb is stationary and while moving. Additionally, these parameter and value data sets ensure that injured tendon and ligaments do not suffer from impingement forces that would prevent tendon and ligament glide within their sheaths that would either cause or worsen a strain or tear. These forces also aid in aligning tendon and ligament fibers while healing to reduce misaligned scar tissue that can lead to impaired tendon or ligament function and chronic lameness.

Unlike prior art, an instance of plurality of the textile may include layers of conductive, semi-conductive Plezio, Resistive, Acoustic, Isolating, Magnetic layer(s), that will render the textile fit as an e-textile with electronics or organic electronics as the embodiments change for purpose of use.

The plurality of lamination and element for equine apparel that reduces or overcomes noted risk of neoprene, leather or other rigid to semi-rigid materials does not currently exist.

The significance of developing the plurality of lamination and element for developing an e-textile for specified parameters and values is paramount. The data that can be collected with an intelligent textile is needed to expand the working knowledge of the equine athlete or equestrian athlete musculoskeletal system for scientific and practical purposes; to aid in the reduction in the incidence of Tendon and Ligament Injuries that can lead to poor performance, lameness or catastrophic joint failures and fracture. It may also aid in reducing the incidence of re-injury that leads to chronic tendonitis, desmitis or osteoarthritis. Data can also aid in the development of stretch materials for the equine with the force vector, force vector return to specifically accommodate their body weight.

The present invention further improves upon the prior art by providing an intelligent textile to aid in defining and implementing parameters and values for non-destructive evaluations. The evaluations can be performed in a manner that does not affect the future usefulness of the body part in which it was applied. To give an example, at present, it is not possible to determine joint force or joint pressure readings without surgically inserting a probe into the subject equine or human joint. Locomotion of the equine or human to determine joint force and pressure readings at each gait, would result in destruction of the joint being tested due to A) surgical destruction and B) mechanical destruction from the probe. The intelligent textile can provide the support and protection needed for application of use, as in the case of performance apparel, with the exemplary embodiment of parameter and value. An example of exemplary embodiment would be monitoring of acoustic emissions, see FIG. 6, during the inventions use on a horse in a customary training situation. When the parameter and value for acoustic emissions hit a parameter and value set, the trainer, rider or handler could stop a performance to prevent an acute injury or delayed onset lameness by noting the sub-clinical micro-edema or micro-tears. Acoustic emissions with another parameter and value and parameter and value data set, would aid in evaluating the soft tissue and joint health of a rehabilitating equine, rider or other athlete being returned to use/work with reduced incidence of reinjury. Another exemplary embodiment would be a fabric stretch sensor to the distal joint of the equine or to a shoulder of a baseball player. As the athlete fatigues, the range of motion of the joints become affected. It a pitcher overthrows; the stretch sensor would trigger notifying that a micro-event has occurred that with continued use, would lead to injury. Much like a hyperextension of the equine fetlock joint would lead to injury if the animal was forced to continue to perform after an onset of fatigue event was signaled.

An example, but not by way of limitation, that may or may not be added to the intelligent textile could be an element that that modulates a frequency that requires low power; to an ultrasonic frequency for a pitch-catch scenario, a pulse-echo, a pulse-echo overlap scenario. To illustrate, see FIG. 6C-D, the orthogonally placed elements can send (pitch) and receive (catch) the modulated frequency. Frequency may include an ultrasound to sound measurement. With yet to be determined parameter and value sets; the parameter and value may or may not give an indication of joint and tissue status. Sound Physics gives us the base parameter and value sets to begin researching parameter and value; parameter and value sets for this application. It is known that the signal (sound) speed will change based on the increase of temperature. It is also known that the signal (sound) will be altered by the density; viscosity; or volume. Therefore using the references points provided by current multiphasic ultrasonic technology as a starting point, one can begin to determine parameter, value and parameter and value data sets for this application. Catching the speed in which the signal crosses the tissues and listening for the change of tone; one can begin to surmise sub-clinical changes to the underlying tissues. The tissues natural inflammatory response will increase the temperature beyond that of normal exercise and sustain it past the exercise recovery period; while exudates or micro edema begin to develop. Therefore, degree of inflammatory changes that may lead to acute injury, damage or breakdown could be detected at a much earlier stage than is currently possible. For the previously injured animal; the tissue recovery can be more closely monitored before returning the animal to duty. To give another illustration that is not to be considered restrictive in nature; the distal limb of the equine is the most fragile and prone to injury, breakdown and fracture. It is in theory possible to place orthogonal elements to triangulate a signal to monitor for micro-tears of the soft tissue, changes in bone density or cracks to find minute changes that are not otherwise visualized by current imaging techniques such as x-ray or standard ultrasound.

The Potential fields of application for these technologies and products include: veterinary and or medical evaluation and or diagnosis and or treatment; sports training and virtual exercise; it is possible to monitor for energy expenditure measurement; rate of fatigue onset while improving balance as the compression will assist with proprioception; improvements to avatar animation; computer and or virtual lameness simulations or diagnostic or predictive injury software or activity simulation such as virtual riding; tele-robotics or telemedicine; powering portable electronic devices under adverse and prolonged conditions; Equine and or human-to-computer interfaces for use in environments without clean flat surfaces; flexible Equine or human-to-computer interfaces; Equine or human-to-computer interfaces for 3D applications involving parameter and value manipulation; and sound masking and sound cancellation for creating localized sound environments for acoustic emission detecting, signaling and or receiving; or such devices in the scope of a computer, a processor, or any other structure. These are not to be construed as limitations to discount the potential for education, communications, military applications, veterinary medicine, medicine, telemedicine, sports medicine and orthotics and orthoses and or prosthetic development.

BRIEF DESCRIPTION OF THE PRESENT INVENTION

A Wearable Orthopedic/Orthotic Device with capability of Diagnostics. Scientific research and testing cites the inherent flaws to Prior Art which may make them undesirable to use. Prior Art has been shown to introduce allergies, heat damage, mechanical injuries and joint interference from material binding, bunching and migrating. Due to inherent flaws of Prior Art, they are not suitable for the plurality of laminations and elements to include fibertronics; organic electronics and other forms of e-textiles.

Unlike prior art, this plurality of textile is specifically designed to meet an unmet medical need for the Equine in Equestrian Sports Medicine, Rehabilitation or Activities. The invention provides specific benefit and addresses a well-defined population of injured horses suffering from lameness whose treatment or diagnosis is not adequately addressed by available therapy or diagnostic.

Unlike prior art, this plurality of textile provides athletic compression and support for sleeves, sports medicine boots, bandages and wraps that can be fashioned for the soft tissue and musculoskeletal system of equines that is non-neoprene. (FIG. 2B)

Unlike prior art, this plurality of textile is suited to aid in the treatment and recovery of a previously injured animal related to the known benefits of compression to reduce edema, swelling and pain associated with injuries. The yieldable resistance (FIG. 4) provides support to the circulatory, lymphatic other soft tissue and musculoskeletal systems (FIG. 5). It is undesirable to disrupt the blood flow or create pressure that can lead to tissue damage or necrosis from applying unyielding boots or too tight of, bandages and/or wraps.

Unlike prior art, this plurality of textile relates to materials that are known to be non-allergenic or hypo-allergenic to prevent or reduce the incidence of allergic reaction and dermatitis. In susceptible horses, ponies and other equines, neoprene can cause a latex type allergic reaction, which has known to be fatal in some instances.

Unlike prior art, the plurality of textile is lightweight and hydrophobic. Neoprene and other prior art articles applied for protection can be comparatively heavy and absorb water. Each additional ounce of fluid absorbed into the prior art, adds an additional seven pounds of strain pressure to the competing equine athlete. This additional strain increases the rate of fatigue, increases the incident for injury (FIG. 5A) up to and including catastrophic joint failures.

Unlike prior art, the plurality of laminations may or may not include a clue mark for visual determination of the compressive force exerted upon application of the apparel (FIG. 4).

Unlike prior art, the plurality of laminate and element (FIG. 1) can not only provide for compression for sports, occupational, recreational and rehabilitation apparel, but can become an e-textile to monitor a parameter from a parameters list and a value from a values list (FIG. 3).

Unlike prior art, the textile is not limited in scope to traditional apparel as a subject matter and the combination of laminate and element are not bound by prior art limitations.

It is expected that the e-textile will be improved (FIG. 3,6) with yet to be used or yet to be invented materials as the field of Fabritronics, wearable computer systems and intelligent fabrics and their interface with other devices in the scope of a computer, a processor, or any other structure that are invented or improved for equine and equestrian sports or activities application. This does not preclude or restrict the use of the intelligent textile for other sports medicine or medical application.

Objects of the Invention

1. It is the general objective of the invention to overcome the inherent flaws and disadvantages of prior art for equine apparel including ankle bracing and wraps.
2. It is a further objective of this invention to provide a protection system, that once it is in place; the clue mark denotes safe application of compression by the end-user.
3. It is a further objective that an embodiment of laminations and elements are suitable: determined from a parameters list and a value to be determined from a values list; thereby describing an item within the classification set of a parameter-value pair.
4. It is a further objective of this invention to have an exemplary embodiment that, as an intelligent textile, can be Fabritronic and may or may not be machine or computer implemented at least in part.
5. It is a further objective of this invention to create a textile that will in part aid in non-destructive evaluation of underlying tissues for living tissues regardless of species.

SUMMARY OF THE INVENTION

These and other objects of this invention are achieved by providing an equine supportive, protective and bandaging system for the joints of locomotion for the equine athlete. The system will be wrapped and secured or introduced onto the limb of the animal without disrupting range of motion (FIG. 7). Unless said disruption is the desired effect for a therapeutic purpose.

The orthotic is in the form of a textile panel of an elastic-dynamic material laminated fabric suitable for use in the manufacture of orthotic devices, garments and the like; or in the manufacture of other body coverings such as bandages and the like. In particular, the invention relates to the use of an expandable laminate that is hypo-allergenic and exhibits enhanced air, vapor transport and heat release through transport characteristics though the thickness thereof (FIG. 2C).

An exemplary embodiment fabric will contain enhanced abrasion resistance for use in equestrian application on the outer surface without disruption to breath-ability, stretch or compression. The inner layer will provide support, transpiration and a soft hand for comfort.

The said embodiment of the invention may or may not have Plezio, Resistive, Acoustic, Isolating, Magnetic layers dependent upon application of use for equine or equestrian sports or activity. The exemplary embodiments are suitable for the development of a fabritronic textile for other sports application or medicine. Numerous variations are possible as will be shown in the description that follows.

Regardless, of what is perceived to be the anatomical effect or treatment; Applicants supports are far more flexible than neoprene. They do not gather, pinch, or bunch into a joint space. There is greater porosity with thermal release than with neoprene without adding additional holes or perforations to weaken the integrity of the materials. Unlike Neoprene, there is no Colophony present to cause contact dermatitis or allergic reaction. In 2009, the American Contact Dermatitis Society gave neoprene the dubious distinction as the allergen of the year. Unlike neoprene whose strength comes from the fabrics bonded to its surface, the polyurethane laminate core does not easily rip or tear, even when intentionally punctured.

As the core has its own strength and support, the materials laminated to the surfaces will provide additional strength and support to the equine than do neoprene products. Due to the built in strength to all layers of the product, there is no significant loss of support and strength in comparison to neoprene.

The thick bulky nature of neoprene, or lack of four-way stretch in other materials like leather, causes bunching and binding when the equine extends into the swing phase of his gait. Neoprene is known to migrate out of place when wet and this migration is amplified under the weight of an equine athlete. Due to the nature of the material being used, the qualities of the material of this invention will overcome many flaws inherent to neoprene's use.

The benefits using this textile to overcome the inherent flaws of neoprene and other bracing, support, bandaging and wrapping materials allows for the additional lamination layers and elements for the e-textile to be achieved with reduced risk and within common acceptance by the end-user.

The inferred supports, wraps and bandages being constructed with the thin, highly elastic breathable material having elastomeric stretch capacity being highly elastic and thin, readily conforms to the proportions of the equine structure it targets for fit. As the limb flexes and extends through the phases of the gait, the material does not bunch or bind into the joint spaces (FIG. 7). Being highly breathable, there is no heat build-up (FIG. 2D) to cause harm to soft tissue structures. Only, the therapeutic body heat is retained due to a more natural thermo-regulation. Due to the porosity of the material, sweat exchange occurs mimicking the body's natural cooling effect (FIG. 2C).

The uniform compressive force reduces the soft tissue oscillations from concussive forces endured during locomotion. Reducing these oscillations prevents micro-traumas that lead to soft tissue damage that causes suffering and injury up to and including catastrophic joint failures. Compression supports the circulatory and lymphatic systems as well as controlling vibrations of the tendons and ligaments. To ensure safe application of compression, a clue-mark may or may not be placed on the material/closure system (FIG. 4).

The materials will be treated to be hydrophobic so there is no water weight gain from sweat, splash or if an equine needs to enter a water obstacle that requires submersion. (Flicks Law of Diffusion) Improved materials, which may or may not be a fiber-metal laminate; may or may not be a high tenacity nylon that is rigid to semi-rigid, for use in impact/strike protections that are lightweight will be additionally applied to the improved material to protect the limbs from blows. At this time, the laminates are being tested and are prototypes for this application.

BRIEF DESCRIPTION OF THE SEVERAL VIEWS OF THE DRAWINGS

FIG. 3 is an illustration showing a compilation of plurality of parameter, value, element example sub-images;
FIG. 3A is an illustration showing a legend;
FIG. 3B is an illustration showing example duty and performance as;
FIG. 3C is an illustration showing example parameter and value sets;
FIG. 3D is an illustration showing an example parameter;
FIG. 3E is an illustration showing an example value;
FIG. 5 is an illustration showing a compilation of distal limb structures sub-images;
FIG. 6 is an illustration showing a compilation of I-textile for potential tissue evaluation sub-images;
FIG. 6A is an illustration showing a legend;
FIG. 6B is an illustration showing a plurality of lamination example;
FIG. 6C is an illustration showing a cross-section of an embodiment of the present invention;
FIG. 6D is an illustration showing a cross-section of an embodiment of the present invention;
FIG. Seven is an illustration showing a compilation of covered equine hind distal joint sub-images;
FIG. 8 is an illustration showing a compilation of known muscle & tendon forces of equine forelimb sub-images;
FIG. 8A is an illustration showing human and equine strike forces.

DESCRIPTION OF EMBODIMENT

Figure 1:
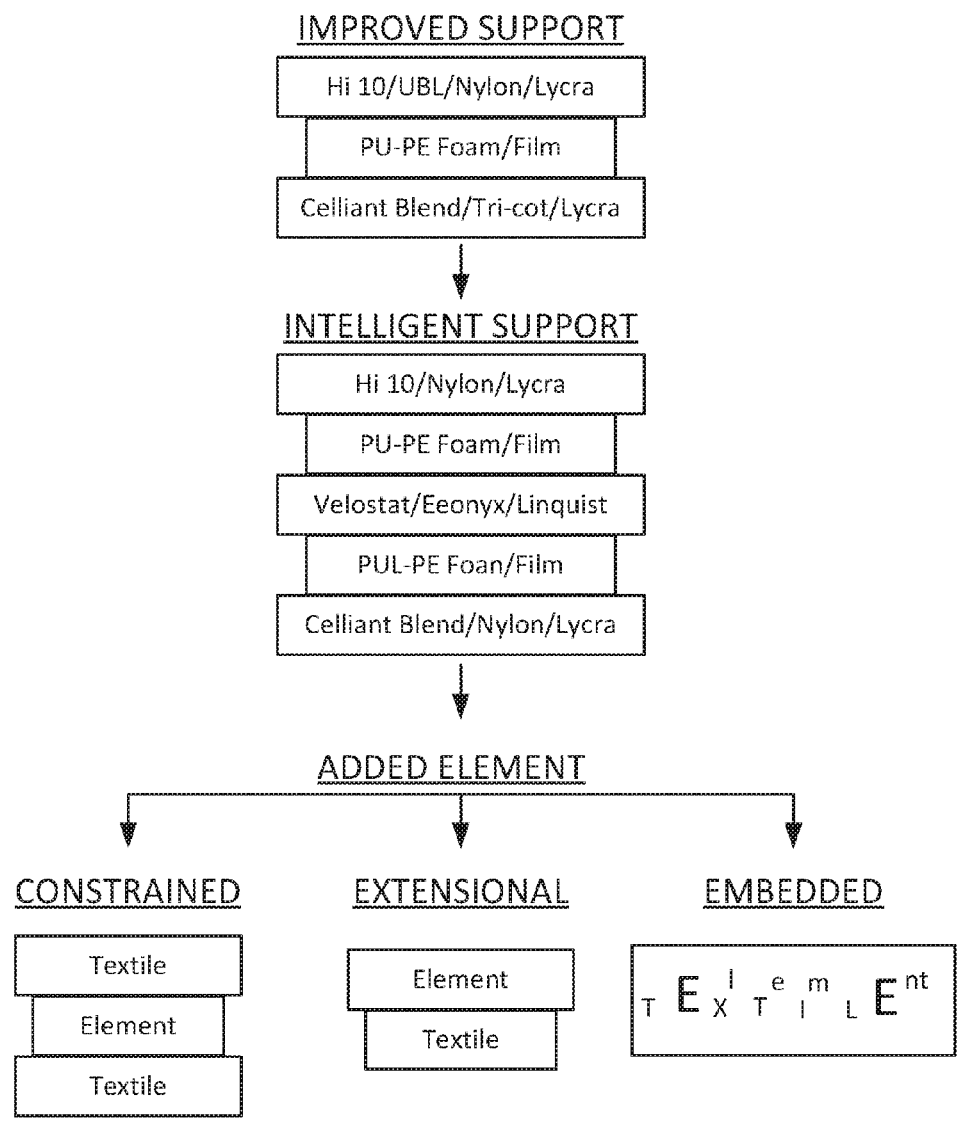
FIG. 1 is a plurality of lamination flowchart.

FIG. 1 is a flow chart which illustrates the plurality of textile embodiments for equine apparel for constructing an improved soft tissue compression support including but not limited to bracing. (7B,C and 6C,D) The material is of at least three elastomeric or stretchable layers that are laminated and/or bonded together in a conventional manner. (2, 3B)The material is bonded in a manner to produce an elastomeric material of desired thickness that stretches in a minimum of one direction, but may be omni-directional. At least one layer is of polyurethane polyether material that stretches in a minimum of one direction, but may be omni-directional. See FIG. 3D of the drawings which illustrates a textile embodiment where an element is added to at least one layer of the laminate to obtain a specified parameter.

See FIG. 3E for embodiment examples for obtaining a specified value. See FIG. 3C for example embodiments to obtain a parameter and value data pair. These drawings are not intended to be limiting of applications for data collection of the e-textile. All known and unknown laminate variations laminated or bonded by a known technique to provide a material that has characteristics that are known to improve equine apparel. An elastomeric laminate material for constructing soft tissue compression support including but not limited to bracing. Elements are not limited to fabritronics and may or may not include a stay, a plate, reinforcements for wear, protection, for fit. The material produced will eliminate or reduce the inherent risks associated with currently available bracing materials such as neoprene, leather and rigid to semi-rigid thermoplastic polyurethanes.

Figure 5A:
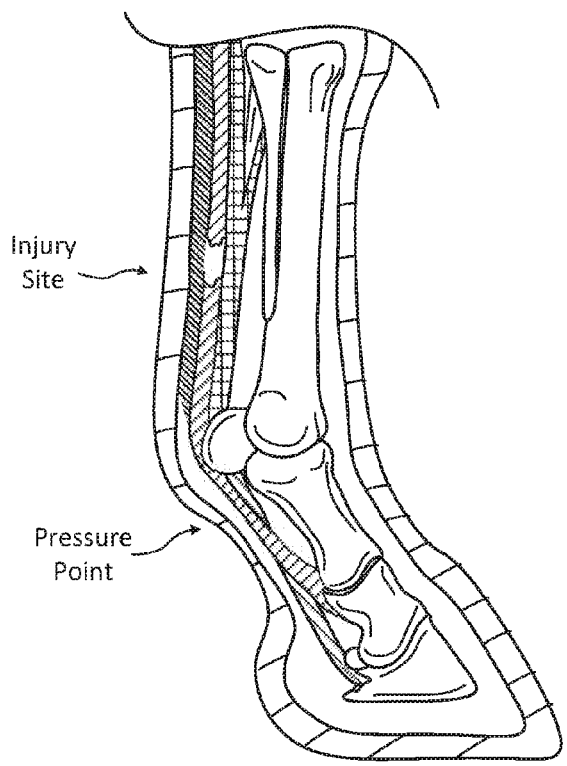
FIG. 5A is an illustration showing injury to a ligament and bind point.
Figure 7A:
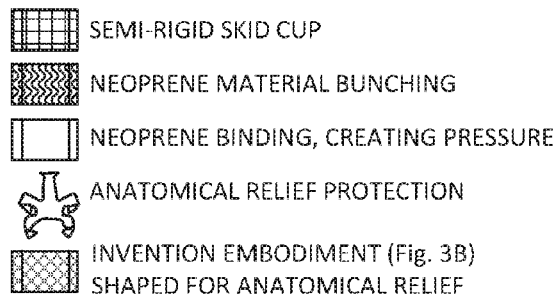
FIG. 7A is an illustration showing a legend.
Figure 7C:
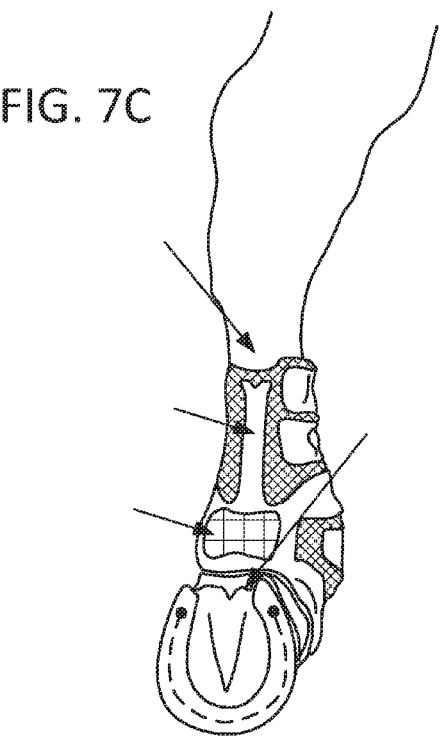
FIG. 7C is an illustration showing an embodiment of the present invention.

Due to the rigidity of leather, rigid to semi-rigid thermoplastic polyurethanes and the like, product design can exert forces into the delicate tissues of the body portion being covered during full range of motion when placed at the FIG. 5A pressure point. Occasionally due to the rigidity, the entire brace can be displaced around the fetlock joint, rendering it useless for its intended purpose. FIG. 7 B shows an illustration of an actual photograph taken of a performance horse in neoprene skids boots on the hind limb. The neoprene is shown bunching, binding and interfering with the joint space as the limb enters the swing phase of equine locomotion. (Plating is for impact or mechanical injury protection. Semi-rigid skid cups are an example of this.)

As the resulting plurality of textiles and elements are thin and pliable, the desired configuration for use can be readily achieved via conventional sewing methods and will not require thermoplastic molding equipment or leather/neoprene sewing machines. Material edges in need of joining can also be bonded via known fabric adhesives, seam welds, laser or ultrasonic welding as is known for conventional textile manufacturing. Sewing notions such as seam binding and sewing thread will match the conductive, insulating and or stretch requirements of the base material to which they are applied. The pliability and stretch of the material permits apparel to be readily conformable to the contours of the equine body parts such as the fetlock joint, hock, knee's and so forth.

Figure 2A:
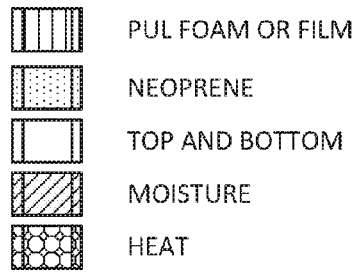
FIG. 2 is an illustration of the prior art.
Figure 2B:
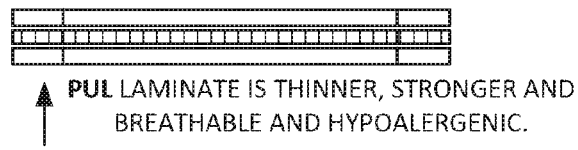
Figure 4:
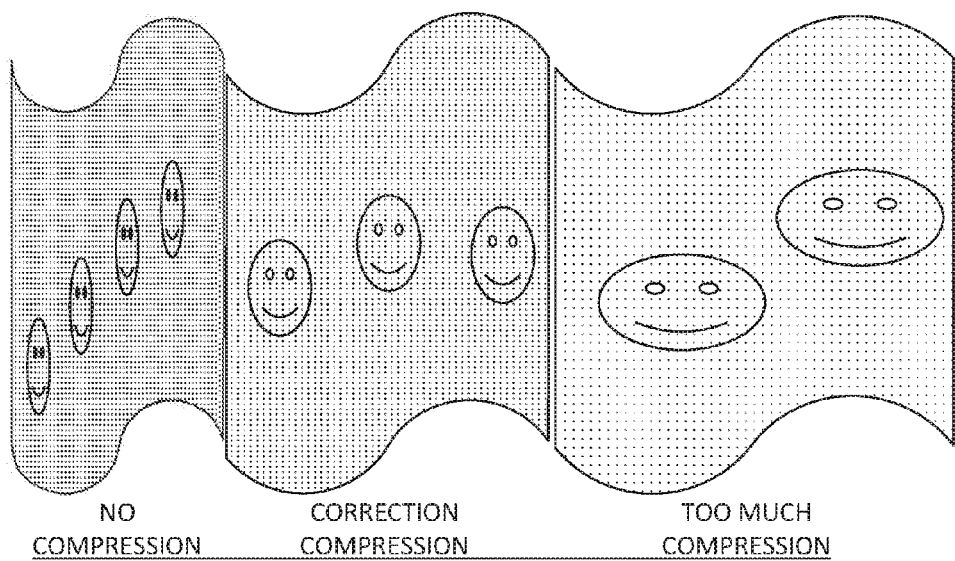
FIG. 4 is an illustration showing a safety clue mark.

FIG. 2B demonstrates, that the plurality of textiles is thinner than traditional neoprene or leather, is more pliable and is therefore, less subject to bunching, binding, migrating and displacement. Unlike neoprene or leather, the stretch capacity and elasticity of the support allows the material to elastically conform to joints during the phases of equine locomotion. Consistency of the uniform resistance and compressive forces will be maintained (FIG. 4) Unlike the Prior Art in FIG. 7B, the ability to cause sheer injuries, restrict blood flow, pinch or cause micro-traumas or edema in the joint is minimized or eliminated in FIG. 7C (with arrows indicating sites of anatomical relief). FIG. 5A, illustrates the pressure point and the most common site of ligament injury in the equine distal limb.

Figure 5B:
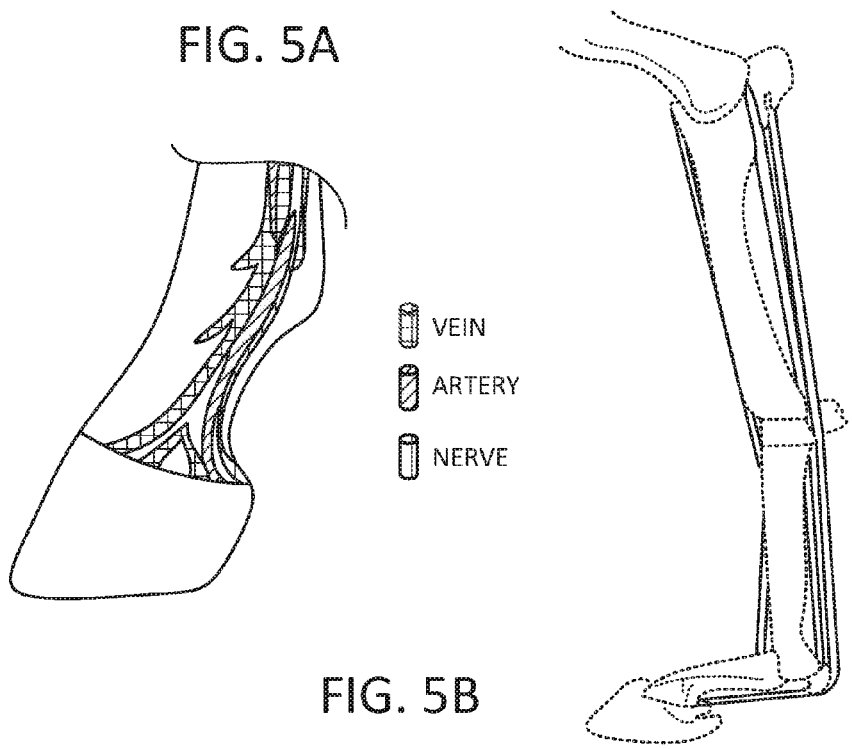
FIG. 5B is an illustration showing a vein, artery, nerve and position.

FIG. 5B shows the blood supply; artery and vein and nerve pathways that can be impacted by pressure exerted onto the distal limb. FIGS. 3C,D,E and FIG. 6 illustrates the means to obtain data to turn the plurality of laminations in FIG. 3B into a body covering such as that in FIG. 7C.

Figure 2C:
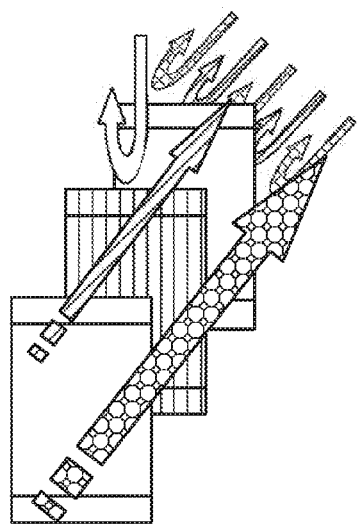
Figure 2D:
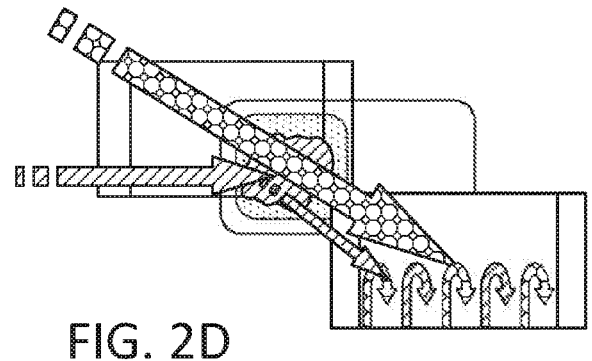

As FIG. 2D illustrates, the plurality of laminated textile with elements requires one to consider the effect on breathability of the material. Neoprene and other materials commonly used for equine apparel and supports are known to cause heat damage to tendon and ligaments in scientific circles. The porosity of the polyurethane reduces that risk in comparison to neoprene, leather and the like does not permit airflow. Some equine products do use perforated neoprene to achieve breathability; however, this lowers the rupture strength, shortens the life cycle and therefore renders a weaker product. The build-up of perspiration and heat can lead to cellular damage and death in the tendon and ligaments of a performing equine. FIG. 2D shows the airflow for traditional neoprene in which a significant number of equine braces commercially available are made. FIG. 2C shows the porosity of the polyurethane, paired with other breathable, stretch materials allows for the body heat to escape and encourages a natural thermo-regulation of the body part in which the material is applied.

FIG. 2D shows that Neoprene does not allow heat or sweat to escape. Unless the outer layer of the neoprene or leather is sealed, they are also subject to diffusion as a result of Flick's Law. Therefore, in addition to the potential for heat related injuries, the wearer is also subject to strain injuries related to water weight gain from diffusion through the neoprene material. FIG. 2C shows that the materials are breathable, will reflect back a therapeutic amount of body heat to allow the soft tissues to be well oxygenated while allowing for an evaporative effect for perspiration and thermoregulation.

Figure 7B:
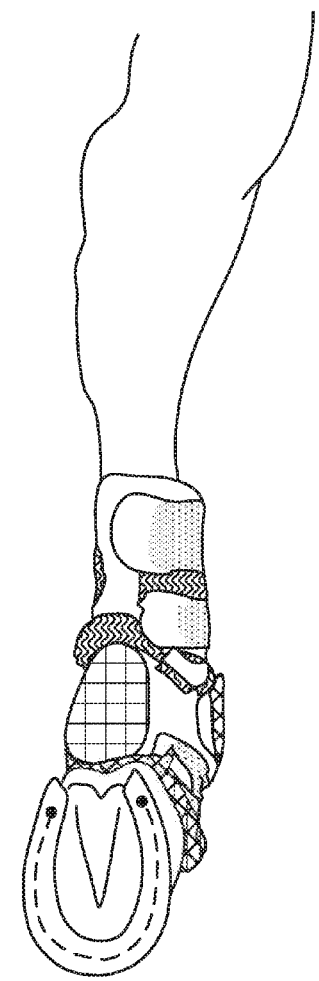
FIG. 7B is an illustration showing prior art.

FIG. 7B shows an example of Prior Art being applied to an equine leg. Regardless of the textile or utility design of equine braces, wraps, supports bandages etc, there is no clue mark to denote safe application. It is up to the end-user to subjectively determine fit on the equine body part in which it is being applied. Other textiles have limited to no ability to contract if the circumference changes. For example, if a textile is applied as a support to a limb with edema and the edema subsides, the textile can slip resulting in a number of other potential types of injury. Such as the horse spooking at a loosened bandaged or sliding down. Slippage can result in the loosened bandage having a tourniquet type effect on the structures it envelopes. When leverage can be applied during the application of a textile, such as in FIG. 7B or in a product as depicted in FIG. 6 and FIG. 7 there is a great potential to incur harm. When greater than 1 to 1 leverage is used, the potential to cause discomfort and harm is even greater. Leverage closure systems like buckles or hook and loop closures that feed through an eyelet and reverses back for closure offer a greater than 1 to 1 force. The vulnerable soft tissues (FIGS. 5A,B) of the equine are placed in even greater compromise when the materials that are being held in place do not have a therapeutic compressive force or stretch to accommodate locomotion. The joint binding, pinching, bunching and the like exert increased forces into the soft tissues.

Whereas items made of this plurality of textile and element such as in FIG. 6 and FIG. 7 would not suffer the same problems. The plurality of textile and element can produce a visual clue for proper compressive fit when applied. The plurality of textile and element can utilize the e-textile for specified parameter and values to prevent or monitor for known causes of injury from inherent risk of textile use, equine sports or activity, repetitive use, occupational, and mechanical injuries and other applications to aid in injury prevention or treatment (FIG. 6). With the addition of conductive thread, sensor or fiber; forces exerted onto or into the tissues from the applied textile can be measured to give location and amount of pressure applied. This can allow for safer development of utility designs collecting data that would show friction, shear and pressure injuries.

This description is not to be considered as limiting to the nature of use of the e-textile. There is potential benefit to monitor tissue changes. As the acoustic emission monitoring has the potential to signal tissues changes regardless of the specie or cause of the inflammatory change.

This plurality of textile readily accommodates ancillary appliances such as brace stays, plates for fetlock (ankle), wraps, sesamoid and patella (on the hock) stabilizers and the like. This invention can take on many forms including strap and pad attachments and the like.

Figure 9A:
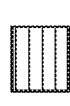
FIG. 9A is an illustration showing multiple embodiments of the present invention.
Figure 9A:
Figure 9A:
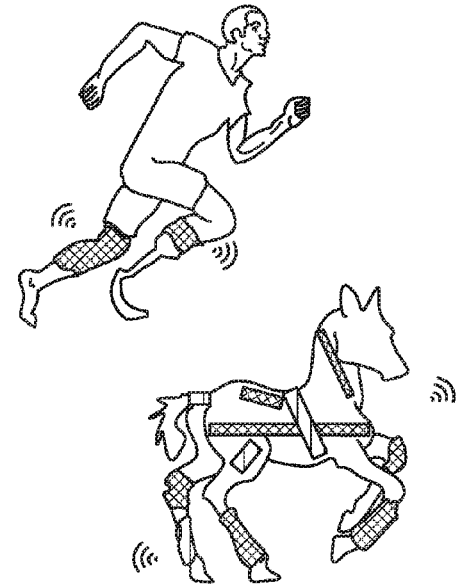
Figure 9B:
FIG. 9B is an illustration of an example portable interface option as according to one embodiment of the present invention.
Figure 9B:
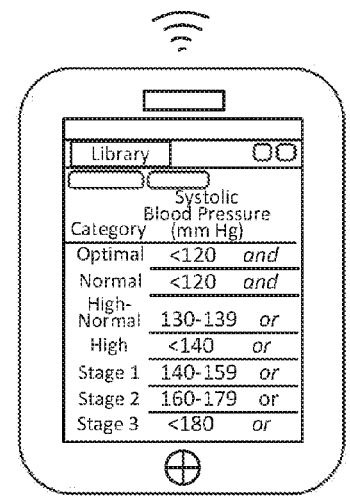
Figure 9C:
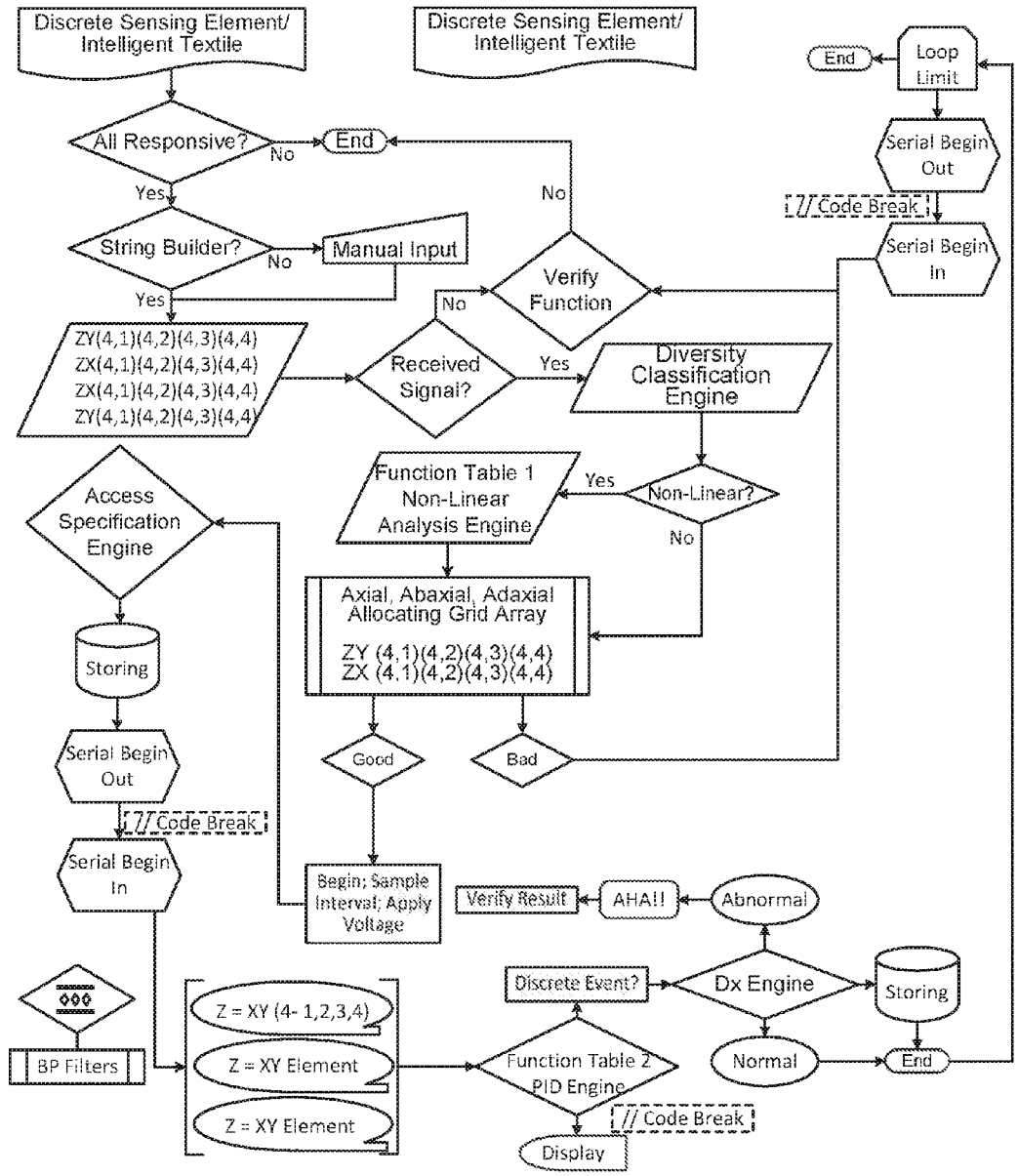
FIG. 9C is an illustration of active and passive sensors with a flowchart for encoding sensors or forming a portion of computer program or product.

An exemplary embodiment of the intelligent textile may or may not have an element that is a computer readable medium or machine-readable medium or such devices in the scope of a computer, a processor or any other structure. Only non-transitory computer-readable media are within the scope of the application. Non-transitory computer-readable media comprise all computer-readable media except for a transitory, propagating signal. It may or may not require the use of an analog/digital converter. It may or may not require the use of a sound modulator. It may or may not be encoded with instructions operable to configure an electronic device to perform methods as described or inferred within the entirely of this document, the code flowchart (FIG. 9C) may form portions of a computer program product. it may or may not include radio-frequency identification, antennae, microchips, micro-processors, speakers, microphones, transducers and other sensors as required. Other embodiments can be used, by one of ordinary skill in the art upon reviewing the descriptions. Additionally, it is understood that an equine has four limbs and therefore creates the context of a network system to utilize a described embodiments in the present specification. Due to a quadruped's unique ability to compensate for injury, all limbs are of interest individually and in sets. Applicant respectfully submits that a person of ordinary skill in the art would readily appreciate that practicable embodiments of the claimed invention would be conducted with the aid of a computing machine, such as a server. Such computing machines are commonly understood to have memory. That operations clearly changes the state of the underlying data since the cache, register, or other memory on which the data is stored must be transformed to have a different magnetic polarity, electrical charge, or the like depending on the technology that is used. These are real physical changes. Further, memory is a real physical article.

Figure 8B:
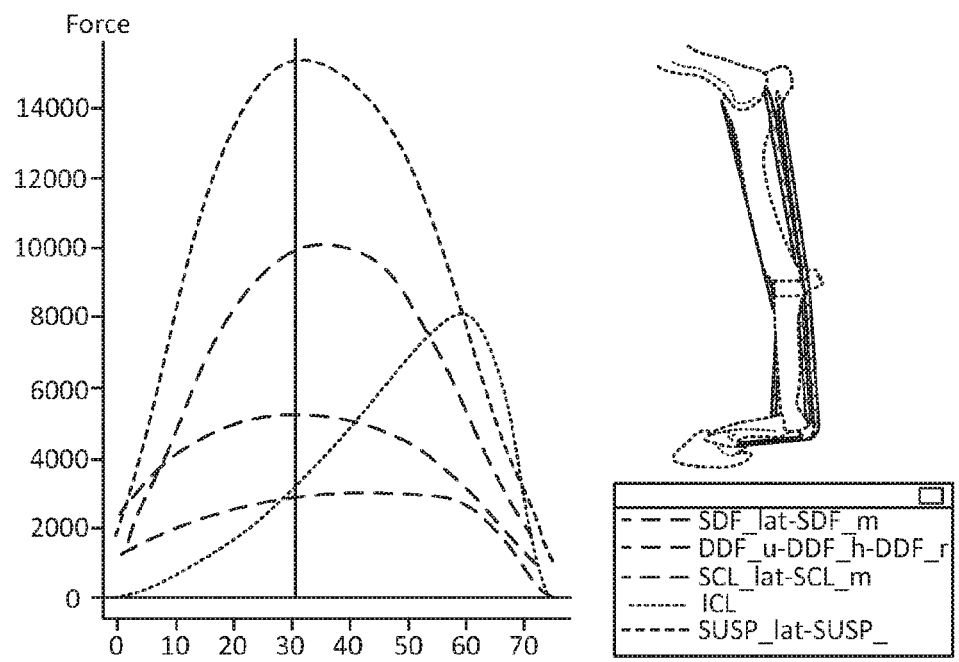
FIG. 8B is a chart showing strike forces.
Figure 8C:
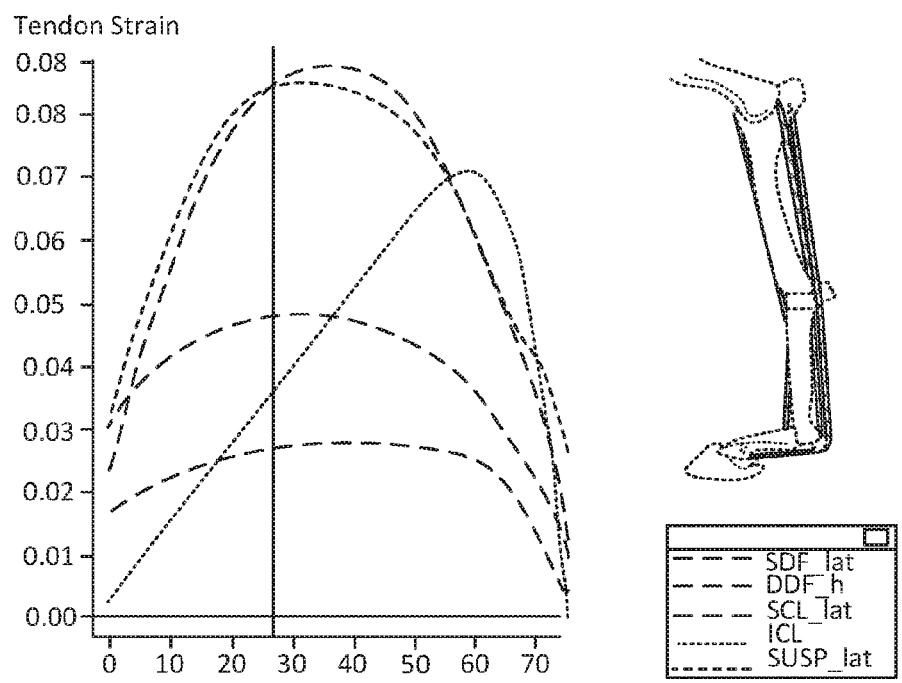
FIG. 8C is a chart showing tendon strain forces;
FIG. Nine is an illustration showing a compilation of further illustrations of I-textile & data interface sub-images.

Whereas the polyurethane layer, polyether layer, bio-rubber and other fabric layer (e.g. Nylon) and elements are known materials, they have not been combined to produce a material as shown in FIGS. 6, 8 and FIG. 11. The material is a modification of certain materials obtained from Textile Companies. Examples of the plurality of laminations involving polyurethane foam, polyether foam, bio-rubber (Yulex) as a replacement for Neoprene, leather and the like. Darlington Fabrics will supply a High Tenacity Nylon. Traditional style numbers are not available at the time of this writing as the product(s) are only available through the Research and Development Lab 63kw10 and its variants, such as Hi10 26880 are intended for use; Polyurethane foam derivatives such as polyether or elastomeric polyurethane foam and film are being trialed Akkas, LLC, item 72020 Wm T Burnett & Co, item RQ 333 10# as well as Bayer Material Science has various foams or films, thickness to specification both under and over 1 mil (0.001 inch) with porosity and required attributes. 3M for Eonyx (or Velostat or Linqstat) stretchable conductive materials and Halogenix LLC for Celliant fiber blends are intended for incorporation in the plurality of laminate. At this time, there are no commercially available versions of these blends as they are proprietary for producing prototype and research items named, Ideal Equine Gear. The final determination of which polyurethane, polyurethane derivative such as polyether foam or film to incorporate; or have custom made, will be determined after prototyping and testing is complete. The scientific best blend may not be commercially viable, if the end-product cost or life cycle cannot fit within the market strain of other commercially available products. At this time, elastomeric or stretchable polyurethane foam does not exist as designed to match loading forces of an equine distal limb. Equines wear materials designed for the athletic support and forces of a human athlete, typically defined as a 150 pound male. Equines, carrying an Equestrian and all tack for a total of 125 pounds, can exert up to 5,100 psi at a full gallop onto their distal limb structures. Whereas, a 150 pound human male can exert 500 psi upon landing a jump on a hard surface from a run to his distal limbs. Textile manufacturers may provide additional treatment to fibers, including but not limited to water repellency while maintaining breathability or silverized for conductivity.

Those skilled in the art will appreciate that variations and modifications may be made without departing from the scope, intent and spirit of the invention. Therefore the invention is not to be limited to the embodiments illustrated and described herein, but are appended as determined by the claims.

Additional Notes

Neoprene and other materials used for performance and rehabilitation wear are limited in scope to determine proper fit, compressive force and feedback. When the end-user removes the products: sheer, abrasion, constrictive injury, heat retention and other inherent risk of use, may or may not have caused tissue death may or may not be seen immediately.

The intelligent textile has the capacity to change some aspects of sports medicine from a subjective to an objective evaluation (FIG. 6). This invention in one exemplary embodiment is an improved textile for supports, bandaging and bracing for human or equine application under harsh conditions subject to abrasion; literally being drug through the water, mud or brush and the like. As previously stated, this invention is designed to overcome flaws found in current products. Additionally, the properties of the invention that makes it ideally suited for supports, bandaging and bracing is what makes it suitable for the exemplary embodiments of an intelligent textile. These exemplary embodiments will also provide data to improve the utility design of products made from the textile embodiments. Piezo-resistive material has two important qualities. First, its resistance through the material decreases when pressured. Second, its resistance across the distance is not affected by pressure and increases with distance. Therefore, sandwiched between two conductive layers; with spacers between, exemplary embodiments can detect both pressure and location. This technique can be used to determine the forces exerted onto the underlying tissues of the applied body part. Improved construction patterns that best accommodates or restrict the full range of motion of the underlying body part can be determined. FIG. 5B has arrows marked A and B. FIG. 5A has a notation signifying the pressure point under the fetlock joint. (Specifically under the sesamoid bone.) Utility design is of a major concern as the fetlock naturally drops (extends) during flexion of the proximal limb to the horizontal level of the heel bulb when a horse is in motion. The elastic strain energy that aids the propulsion of the equine then causes the hoof to snap upwards towards the fetlock as the limb enters the swing phase of gait. As FIG. 7B shows, flexion of the distal joint causes fetlock semi-rigid cups to bind between the heel bulb and the fetlock. With constant motion, there is repeated insult to underlying tissues. When Flexion of the fetlock joint occurs, FIG. 5A shows the pressure point that can be of concern as the distal limb flexes into the applied materials. Therefore, the plurality of lamination and the utility design have an effect on the underlying tissues and if too rigid, unyielding, bunching or binding, can lead to injury in and of itself.

Additionally, the exemplary embodiment of an intelligent textile will provide features not found in other human or equine compression support, bracing and the like. (FIGS. 3,6,7)

The plurality of textile embodiments can monitor for concerns specified by the end-user. For instance, an endurance rider may want to purchase a lightweight, breathable compression support to delay the onset of fatigue in their equine athlete, but may also want the invention to give a visual change via the intelligent textile, were the internal temperatures of the underlying tissues began to approach dangerous levels.

Another exemplary embodiment may utilize the compressive garment to block out external noises via noise cancellation or the like; while listening for acoustic emissions of the underlying body part for changes. To give context; it would be like listening for the change of tone, pitch, sound when stressing a guitar string for tuning and/or de-tuning Or like listening to the sounds emitted by a wooden stick when being stressed prior to it fracturing. While yet another embodiment may monitor for underlying tissue health by measuring the speed and frequency of sound traveling through the underlying tissues to note changes in integrity or inflammation by sending and receiving acoustic emissions. The concept would be to listen for changes as opposed to being able to visualize changes thereby opening up the ability to objectively evaluate tissues and tissue health at what is currently not possible in a sub-acute circumstance.

The proof of concept is readily accepted in sound physics. Unique reference signals are to be determined for bone, ligament, tendon, joint fluid and the like. The speed of sound changes based on temperature and density. It may be possible to take precision velocity measurements of longitudinal or shear (transverse) waves and the like using an exemplary embodiment of FIG. 6. Electromagnetic-acoustic transducers may or may not also be an added element for differential velocity measurements to a specified area to detect a flaw in the underlying tissues. Consideration must be given for Lorentz Forces, Fourier Transform-Phase-Slope determinations; sound refraction (Snell's Law), attenuation and the like before viability of sophisticated Intelligent Textiles are produced.

Modern thermography testing on living tissue shows that acute injury produces heat and chronic injury shows a reduced body temperature to the effected part. Furthermore, the speed and sound frequency changes based on density or viscosity of the medium in which the sound waves passes through or reflects-off. Therefore, it is possible to determine sub-clinical changes that may lead to the onset of injury, monitor the rate of healing and may help reduce the incidence of re-injury by developing parameter and value sets monitored by the intelligent textile. Utilizing sound physics and basic music theory, it may be possible to further distinguish the characteristics of the changes utilizing ultrasound-to-sound. Once reference signals (natural frequency and harmonics) are determined for tissue structures, the character of density changes can be determined. In other words, does the excitation frequency match the natural frequency? For illustration purposes, a normal ligament attachment may resonate a middle C note. An attachment with a micro-tear and micro-edema may resonate a high C. Whereas a ligament attachment with increased density; due to mechanical stress and micro-edema, may resonate a low C. The precision velocity measurements paired with musical modulation will give precise location of flaw, inflammatory and/or density changes and their characteristics. In the words of Oscar Hammerstein II, "A bell is not a bell 'til you ring it."

It is accepted that due to energy consumption requirements; some elements may or may not be added to the intelligent textile and may be used separately or in conjunction with the wearable textile. The concept of having an intelligent textile that is a compressive support or brace that can objectively measure the status of the underlying areas it is wrapped around or covered has even more added value for distal limb products. Including improving the fit and comfort of artificial limbs to amputee's who wish an improved fit for use in active lifestyles. It is accepted due to weight restrictions, the wearable textile may be limited to collection of biometrics pending the development of nano-systems to accommodate a low power, lightweight wearable computer system. Thus, a separate system may be needed to achieve this goal.

This would have great impact on all forms of human and veterinary sports medicine, medicine, among other applications for determining fit and wear of compressive devices. For example: Neoprene wraps for equines become less compressive and the neoprene becomes brittle with aging. Without tearing apart the item, as long as the Lycra appears to be intact; the end-user continues to use the equipment that has been rendered less effective or ineffective due to age; the intelligent textile, potentially, could signal the end-user of such ineffectiveness for replacement.

Another example for illustration purposes for the usefulness of such a device for the protection of a medicated injured athlete be that athlete a human or an animal. Football players, baseball players, golfers and many other athletes play their sport with soft tissue injuries the same as a horse competes. With the lack of evidence to support sidelining the athlete and an effective pain management program in place, the athlete may appear ready to return to duty. The e-textile would be able to evaluate the underlying body part to detect sub-clinical inflammation or defect that would portend re-injury or catastrophic tissue failure.

Current technology for joint and sports health has limitations as imaging is the basis of the evaluation, assessment or diagnostic protocols, such as the use of X-rays, MRI's and the like. Anyone who has been subject to an "Exploratory Surgery" is keenly aware that ultrasound, x-ray, MRI, PET Scans and Nuclear or Radiographic Uptake imaging has its limitations and therefore a surgeon must occasionally operate to go in and see what is wrong. Even with the direct visualization, the surgeon cannot see an inflammatory response, micro-edema, micro-tear, or micro-growth that is the source of pain or other symptomology.

The ability to detect and change the definition of sub-clinical to clinical injury although the athlete appears sound, may prevent many catastrophic joint failures and the onset of chronic medical conditions. Equine and child athletes are still developing when compelled into sporting activities by authority figures. Both suffer compulsory participation as current technology does not support the observed behavior change (resistance) that indicates a sub-clinical injury that portends acute incident. Equines are incapable of vocalizing pain and young children may not have yet developed the language skills to express what they are feeling. Portable, cost-effective systems with no radiation exposure will open up access to care and aid in the prevention of injury and improve outcomes for rehabilitating patients. The impact of detecting what are now sub-clinical changes for repetitive-use sports or occupational changes has far-reaching effects in the human and equine worlds. Such technology development can mitigate the economic impact and loss of equine life from what are now undetectable changes that lead to acute injury up to and including catastrophic joint failure and fracture.

The invention is a wearable orthopedic/orthotic device with capability of diagnostics. Unlike other wearable solutions on the market, this plurality of lamination allows for bracing to become intelligent bracing by overcoming flaws in Prior Art that would preclude safe application of additional elements. This device can demonstrate the power of harnessing both clinical and sub-clinical personal health information to better manage injuries that lead to pathology or disease states across the patients' health continuum. A plurality of laminate for equine limb wear intended for unmet medical needs in equine limb and ankle bracing systems in equestrian sports medicine, rehabilitation or activity. The embodiments derived from the laminate offers significant, clinically meaningful advantages in the mitigation and diagnostic monitoring of life-threatening or irreversibly debilitating disease or condition of the equine limb that has suffered lameness with tendon and ligament injury. The above descriptions are intended to be illustrative and not restrictive. Also, in the above description, features may be grouped together for ease of disclosure. This is not meant to be interpreted to mean than an undisclosed feature is essential to any claim. The subject matter is conceptual to the textile development and the inventive subject matter may lie in less than of features of a particular disclosed embodiment. The above-described examples, or aspects thereof, may be used in combination with each other. It is accepted that due to energy consumption requirements; some elements may or may not be added to the intelligent textile and may be used separately or in conjunction with the wearable textile to obtain parameter, value or parameter and value data sets. For illustration, a parameter and value set may include measuring the temperature of the applied device in relation to the limb temperature to signal the need for removal to prevent overheating issues related to thermoregulation between the product and the underlying tissues. This parameter and value set may signal the need for a therapeutic treatment option such as removing the appliance to air the limb or cold hosing the limb to return the limb to tissue safety thresholds. Another illustrative parameter and value set may be the determination of passive moment-angle joint relationships with active-joint angle relationships between injured (value) and non-injured limbs (parameter). While the tissue oscillations can be determined by monitoring for changes (value) to inherent resonance (parameter). These data sets can inform kinematics or reverse kinematics as it relates to biomechanics and locomotion. This will inform value and parameter data sets when monitoring for compensatory gait patterns in the quadruped. This is a significant data for sub-clinical injury detection and diagnosis. Only non-transitory computer-readable media are within the scope of the application. Non-transitory computer-readable media comprise all computer-readable media except for a transitory, propagating signal. It is submitted with the understanding that that it will not be used to interpret or limit the scope and meaning of the claims.

The above descriptions are intended to be illustrative and not restrictive. Also, in the above description, features may be grouped together for ease of disclosure. This is not meant to be interpreted to mean than an undisclosed feature is essential to any claim. The subject matter is conceptual to the textile development and the inventive subject matter may lie in less than of features of a particular disclosed embodiment. The above-described examples, or aspects thereof, may be used in combination with each other. It is accepted that due to energy consumption requirements; some elements may or may not be added to the intelligent textile and may be used separately or in conjunction with the wearable textile to obtain parameter, value or parameter and value data sets. It is submitted with the understanding that that it will not be used to interpret or limit the scope and meaning of the claims.

What is claimed is:

1. An equestrian soft tissue compression support with diagnostic and therapeutic capabilities, the equestrian soft tissue compression comprising: a soft tissue compression material with a passive resistance to expansion and a low active compression force; and,
   a sheet of stretchable laminate material formed to wrap at least a portion of an equine appendage or body part, the sheet of stretchable laminate material comprising:
   a stretchable polyurethane membrane; and an elastomeric stretchable material bonded to the stretchable polyurethane membrane, wherein the equestrian soft tissue compression support is configured to wrap at least a portion of an equine appendage or body part, wherein the thickness of the sheet of stretchable laminate material is defined based on the equine appendage or body part being wrapped and exposure conditions, of said equine appendage or body part, the sheet of stretchable laminate material further comprising: an intelligent textile, the intelligent textile comprising: a plurality of conductive fibers; at least one sensor configured to provide at least one measure of at least one parameter associated with a motion of said equine appendage or body part and an effect of said equestrian soft tissue compression support on said equine appendage or body part; and a processor for processing the at least one measure of least one parameter associated with a motion of said equine appendage or body part and an effect of said equestrian soft tissue compression support on said equine appendage or body part; and
   a wireless transmitter for transmitting, via a wireless connection, the at least one measure of least one parameter associated with a motion of said equine appendage or body part and an effect of said equestrian soft tissue compression support on said equine appendage or body part to an external receiver.

2. The equestrian soft tissue compression support of claim 1, wherein the stretchable polyurethane membrane comprises: a porous and breathable polyurethane membrane material configured to allow perspiration and an amount of heat from said equine appendage or body part to escape and to reflect back a therapeutic amount of heat from said equine appendage or body part.

3. The equestrian soft tissue compression support of claim 2 wherein the intelligent textile is configured to provide a visual clue pertaining to at least one of a proper compression fit and an internal temperature approaching a dangerous level.

4. The equestrian soft tissue compression support of claim 1 wherein the at least one sensor comprises an acoustic sensor configured to emit an acoustic signal into the underlying tissue of the equine appendage or body part onto which the equestrian soft tissue compression support is wrapped around, the acoustic sensor further configured to detect a resulting speed and frequency of sound traveling through underlying tissue onto which the acoustic signal is emitted.

5. The equestrian soft tissue compression support of claim 1 wherein the plurality of conductive fibers include fibers for sensing the bend, stretch, flex, force and pressure exerted by the equestrian soft tissue compression support.

6. The equestrian soft tissue compression support of claim 1 wherein the intelligent textile is configured to monitor temperature of the underlying tissue onto which the equestrian soft tissue compression support is wrapped around.

7. A method of monitoring a tissue health of an equine limb, comprising:
providing an equestrian soft tissue compression support with diagnostic and therapeutic capabilities; wrapping at least a portion of an equine appendage or body part with said equestrian soft tissue compression support, wherein equestrian soft tissue compression support comprises: a soft tissue compression material with a passive resistance to expansion and a low active compression force; and, a sheet of stretchable laminate material formed to wrap at least a portion of an equine appendage or body part, the sheet of stretchable laminate material comprising: a stretchable polyurethane membrane; and an elastomeric stretchable material bonded to the stretchable polyurethane membrane, wherein the thickness of the sheet of stretchable laminate material is defined based on the equine appendage or body part being wrapped and exposure conditions said equine appendage or body part, the sheet of stretchable laminate material further comprising: an intelligent textile, the intelligent textile comprising:
a plurality of conductive fibers; at least one sensor configured to provide at least one measure of at least one parameter associated with a motion of said equine appendage or body part and an effect of said equestrian soft tissue compression support on said equine appendage or body part;
and a processor; and a wireless transmitter; the method of monitoring a tissue health of an equine limb further comprising: measuring, with the intelligent textile, of at least one parameter associated with a motion of said equine appendage or body part and an effect of said equestrian soft tissue compression support on said equine appendage or body part; processing, with the processor, at least one measure of least one parameter associated with a motion of said equine appendage or body part and an effect of said equestrian soft tissue compression support on said equine appendage or body part, wherein the processing includes: determining from the at least one measure of the at least one parameter a force exerted onto or into a tissue underlying said equine appendage or body part; and determining, from the force exerted, a location and an amount of pressure applied on said equine appendage or body part; the method of monitoring a tissue health of an equine limb further comprising:
transmitting via the wireless transmitter the at least one measure of least one parameter associated with a motion of said equine appendage or body part and an effect of said equestrian soft tissue compression support on said equine appendage or body part to an external receiver.

8. The method of monitoring a tissue health of an equine limb of claim 7 further comprising: emitting, via an acoustic sensor, an acoustic signal into the underlying tissue of the equine appendage or body part onto which the equestrian soft tissue compression support is wrapped around, detecting, via the acoustic sensor, a resulting speed and frequency of sound traveling through underlying tissue onto which the acoustic signal is emitted.

9. The method of monitoring a tissue health of an equine limb of claim 7 further comprising sensing, via the intelligent textile, the bend, stretch, flex, force and pressure exerted by the equestrian soft tissue compression support.

10. The method of monitoring a tissue health of an equine limb of claim 7 further comprising monitoring, via the intelligent textile, the temperature of the underlying tissue onto which the equestrian soft tissue compression support is wrapped around, and providing, via the intelligent textile, a visual clue pertaining to at least one of a proper compression fit and an internal temperature approaching a dangerous level.

11. The method of monitoring a tissue health of an equine limb of claim 3 further comprising providing, via the intelligent textile, a visual clue pertaining to at least one of a proper compression fit and an internal temperature approaching a dangerous level.

* * * * *